(12) United States Patent
Nakashima et al.

(10) Patent No.: US 8,562,525 B2
(45) Date of Patent: Oct. 22, 2013

(54) BIOLOGICAL SIGNAL PROCESSING APPARATUS, BIOLOGICAL SIGNAL PROCESSING METHOD, AND BIOLOGICAL SIGNAL PROCESSING PROGRAM

(75) Inventors: Yusaku Nakashima, Tokyo (JP); Takashi Tomita, Kanagawa (JP); Seiji Wada, Kanagawa (JP)

(73) Assignee: Sony Corporation, Tokyo (JP)

( * ) Notice: Subject to any disclaimer, the term of this patent is extended or adjusted under 35 U.S.C. 154(b) by 149 days.

(21) Appl. No.: 13/115,367

(22) Filed: May 25, 2011

(65) Prior Publication Data

US 2011/0306895 A1 Dec. 15, 2011

(30) Foreign Application Priority Data

Jun. 10, 2010 (JP) ................................. 2010-133109

(51) Int. Cl.
*A61B 5/00* (2006.01)

(52) U.S. Cl.
USPC .......................................... 600/300; 600/544

(58) Field of Classification Search
USPC .................................. 600/544, 545
See application file for complete search history.

(56) References Cited

U.S. PATENT DOCUMENTS

2010/0106043 A1* 4/2010 Robinson et al. ............. 600/544

FOREIGN PATENT DOCUMENTS

| JP | 2004-350797 | 12/2004 |
|----|-------------|---------|
| JP | 2006-110234 | 4/2006 |

OTHER PUBLICATIONS

Willey et al., "Computer Signal Processing of Long Duration Biotelemetric Brain Data," Biotelemetry (1975) vol. 2, Issue: 6, pp. 329-340. (12 pages).
Anderer et al., "Artifact Processing in Computerized Analysis of Sleep EEG—A Review," Neuropsychobiology (1999) vol. 40, Issue: 3, pp. 150-157. (8 pages).
Anderer et al., "Artifact Processing in Topographic Mapping of Electroencephalographic Activity in Neuropsychopharmacology," Psychiatry Research: Neuroimaging, vol. 45, Issue 2, Aug. 1992, pp. 79-93. (15 pages).
European Patent Office, Extended European Search Report, issued in connection with European Patent Application No. 11004077.1, mailed on Oct. 25, 2011 (8 pages).

* cited by examiner

*Primary Examiner* — Patricia Mallari
*Assistant Examiner* — Etsub Berhanu
(74) *Attorney, Agent, or Firm* — K&L Gates LLP (57) ABSTRACT

A biological signal processing apparatus includes an obtaining unit that obtains a spectrum of a biological signal that has been obtained, a generation unit that generates a three-dimensional waveform by plotting elements of the spectrum obtained by the obtaining unit in a space defined by a time axis, a frequency axis, and an intensity axis, and a detection unit that detects a specified waveform component using a position along the intensity axis at which a cross-section of the three-dimensional waveform in a time-frequency domain generated by the generation unit is to be observed and a state of the cross-section at the position as criteria for recognition.

7 Claims, 8 Drawing Sheets

BIOLOGICAL SIGNAL PROCESSING APPARATUS, BIOLOGICAL SIGNAL PROCESSING METHOD, AND BIOLOGICAL SIGNAL PROCESSING PROGRAM

CROSS REFERENCES TO RELATED APPLICATIONS

The present disclosure claims priority to Japanese Priority Patent Application JP 2010-133109 filed in the Japan Patent Office on Jun. 10, 2010, the entire contents of which are hereby incorporated by reference.

BACKGROUND

The present disclosure relates to a biological signal processing apparatus, a biological signal processing method, and a biological signal processing program that are suitable for use in, for example, a technical field in which a brain wave is measured or analyzed.

A wave (brain wave) transmitted from a brain is observed as a change in the electric potential between electrodes provided at certain positions on a head. In general, a characteristic waveform component such as an alpha wave included in the observed waveform can be visually recognized.

However, a change (hereinafter may be referred to as an artifact) in electric potential due to a component of a wave other than a brain wave is inevitably superimposed upon the brain wave. Therefore, it takes expertise to successfully recognize a characteristic waveform component in a brain wave to which artifacts have been mixed.

A detection technology has been disclosed in which an artifact that exhibits a specific waveform is focused upon and the artifact is detected using a special calculation, and an extraction technology has been disclosed in which a relative value of an alpha wave is extracted by performing a calculation using the results (periodogram components) of a frequency analysis (for example, Japanese Unexamined Patent Application Publication No. 2004-350797).

SUMMARY

In the above-described detection technology, however, artifacts other than a particular artifact that exhibits a specific waveform are not recognized.

On the other hand, in the above-described extraction technology, as can be seen from a description that electromyograms other than that of a brain wave are obtained simultaneously, it is difficult to judge whether a relative value of an alpha wave actually depends on the alpha wave or is caused by an artifact, unless biological signals other than the brain wave are simultaneously observed. In addition, in the above-described extraction technology, it is difficult to simultaneously recognize an alpha wave and other components of the brain wave.

It is desirable to provide a biological signal processing apparatus, a biological signal processing method, and a biological signal processing program that can improve the recognition accuracy of a particular waveform component.

According to an embodiment of the present disclosure, there is provided a biological signal processing apparatus including an obtaining unit that obtains a spectrum of a biological signal that has been observed, a generation unit that generates a three-dimensional waveform by plotting elements of the spectrum obtained by the obtaining unit in a space defined by a time axis, a frequency axis, and an intensity axis, and a detection unit that detects a specified waveform component using a position along the intensity axis at which a cross-section of the three-dimensional waveform in a time-frequency domain generated by the generation unit is to be observed and a state of the cross-section at the position as criteria for recognition.

In addition, according to an embodiment of the present disclosure, there is provided a biological signal processing method including obtaining a spectrum of a biological signal that has been observed, generating a three-dimensional waveform by plotting elements of the spectrum obtained in the obtaining in a space defined by a time axis, a frequency axis, and an intensity axis, and detecting a specified waveform component using a position along the intensity axis at which a cross-section of the three-dimensional waveform in a time-frequency domain generated in the generating is to be observed and a state of the cross-section at the position as criteria for recognition.

In addition, according to an embodiment of the present disclosure, there is provided a biological signal processing program that causes a computer to obtain a spectrum of a biological signal that has been observed, generate a three-dimensional waveform by plotting elements of the spectrum obtained in the obtaining in a space defined by a time axis, a frequency axis, and an intensity axis, and detect a specified waveform component using a position along the intensity axis at which a cross-section of the three-dimensional waveform in a time-frequency domain generated in the generating is to be observed and a state of the cross-section at the position as criteria for recognition.

Although the position along the intensity axis at which a cross-section of the three-dimensional waveform in the time-frequency domain is to be observed depends on the type of waveform component that has been specified, the position does not change even if an artifact has been superimposed. On the other hand, the state of the cross-section of the three-dimensional waveform in the time-frequency domain undesirably changes in accordance with an artifact. However, it is highly unlikely that all the elements such as the position along the axis, the size, and the shape of the cross-section change, and it has been confirmed that at least one element, which is, for example, the position, the size, or the shape that depends on the specified waveform component, is kept unchanged.

Therefore, by using the position along the intensity axis at which the cross-section of the three-dimensional waveform in the time-frequency domain is to be observed and the state of the cross-section at the position as the criteria for recognition, the specified waveform component can be recognized regardless of the type of artifact even if biological signals other than a biological signal of the target of observation are not obtained simultaneously.

In addition, if two types of waveform components have been specified, when the state of a cross-section at a position of intensity that depends on each of the two types of waveform components is observed in the three-dimensional waveform, the characteristics of the waveform components to be recognized can be observed with regard to at least one element, which is, for example, the position, the size, or the shape of the cross-section. Therefore, even if the two types of waveform components are mixed together in the same period of observation, the waveform components can be simultaneously recognized.

Thus, a biological signal processing apparatus, a biological signal processing method, and a biological signal processing program that can improve the recognition accuracy of a particular waveform component can be realized.

Additional features and advantages are described herein, and will be apparent from the following Detailed Description and the figures.

DETAILED DESCRIPTION

Embodiments of the present application will be described below in detail with reference to the drawings.

Figure 1:
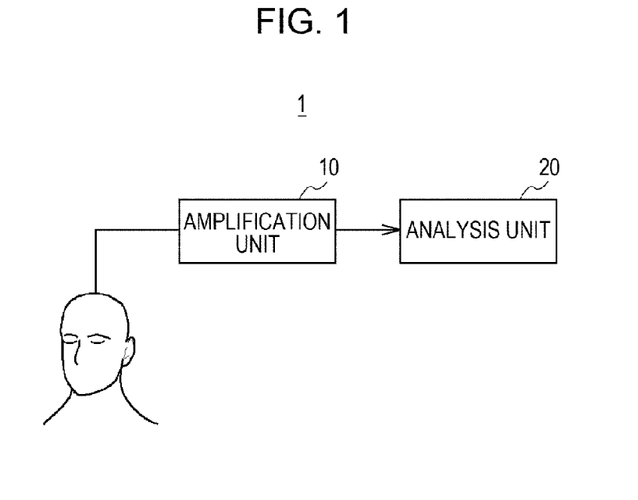
FIG. 1 is a block diagram illustrating the configuration of a biological signal processing apparatus.

1. Embodiment
1-1. Configuration of Biological Signal Processing Apparatus
1-2. Configuration of Analysis Unit
1-3. Functional Configuration of Brain Wave Processing
1-4. Procedure for Brain Wave Processing
1-5. Advantageous Effects
2. Other Embodiments
1. Embodiment
1-1. Configuration of Biological Signal Processing Apparatus FIG. 1 illustrates a biological signal processing apparatus 1. The biological signal processing apparatus 1 includes an amplification unit 10 and an analysis unit 20.

The amplification unit 10 observes a wave transmitted from a brain as a change (hereinafter may be referred to as a brain wave signal) in the electric potential between a probe electrode provided at a certain position on a head and a reference electrode provided at a position other than one on the head, and amplifies the brain wave signal.

The analysis unit 20 is configured to perform various processes on the brain wave signal obtained as a result of the amplification performed by the amplification unit 10, and to display and hold the results of the processes.

1-2. Configuration of Analysis Unit

Figure 2:
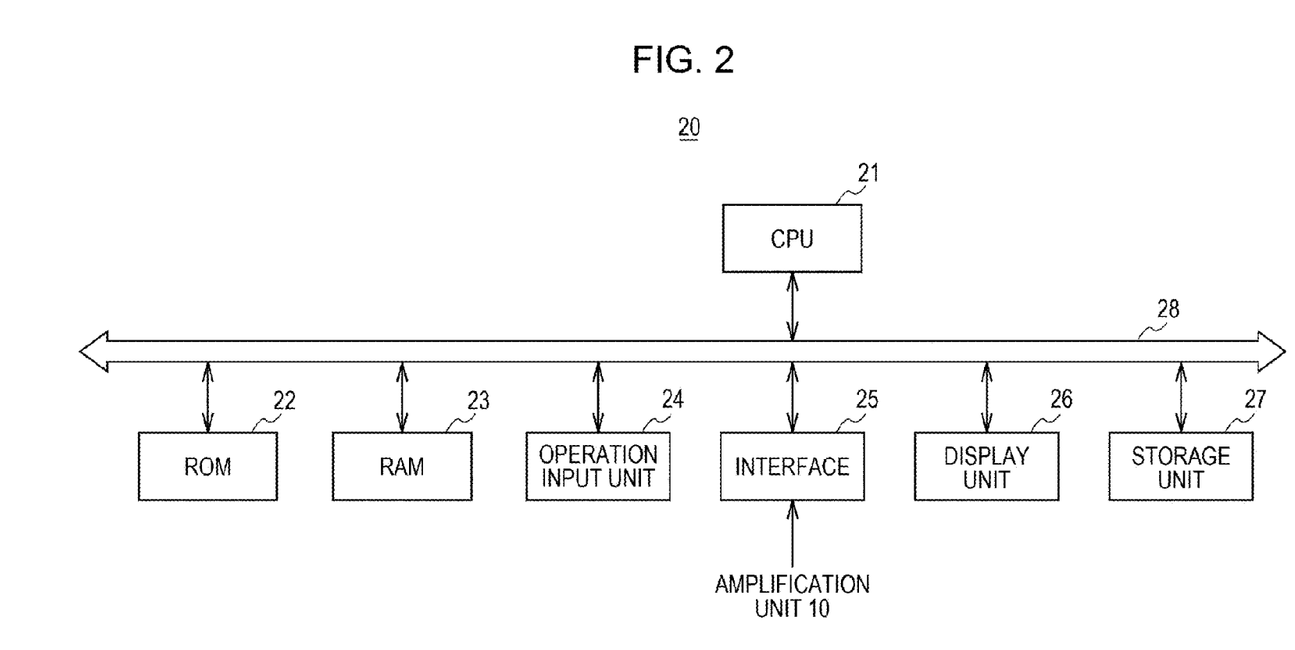
FIG. 2 is a block diagram illustrating the configuration of an analysis unit.

The analysis unit 20 is configured by connecting various pieces of hardware to a central processing unit (CPU) 21 that is responsible for control as illustrated in FIG. 2.

More specifically, for example, a read-only memory (ROM) 22, a random-access memory (RAM) 23 that serves as a work memory of the CPU 21, an operation input unit 24 that inputs an instruction corresponding to an operation performed by a user, an interface 25, a display unit 26, and a storage unit 27 are connected through a bus 28.

The ROM 22 stores programs for executing various processes. The amplification unit 10 is connected to the interface 25.

The display unit 26 may be a liquid crystal display, an electroluminescence (EL) display, a plasma display, or the like. In addition, the storage unit 27 may be a magnetic disk typified by a hard disk (HD), or may be a semiconductor memory, an optical disk, or the like. A portable memory such as a Universal Serial Bus (USB) memory or a Compact Flash (CF) memory may be adopted, instead.

From among a plurality of programs stored in the ROM 22, the CPU 21 expands, into the RAM 23, a program corresponding to an instruction issued from the operation input unit 24, a module, or the like. The CPU 21 then controls the display unit 26 and the storage unit 27 as necessary in accordance with the expanded program.

1-3. Functional Configuration of Brain Wave Processing

In this embodiment, upon receiving a brain wave signal from the amplification unit 10 through the interface 25, the CPU 21 expands, into the RAM 23, a program (hereinafter may be referred to as a biological signal processing program) relating to processing of a biological signal.

Figure 3:
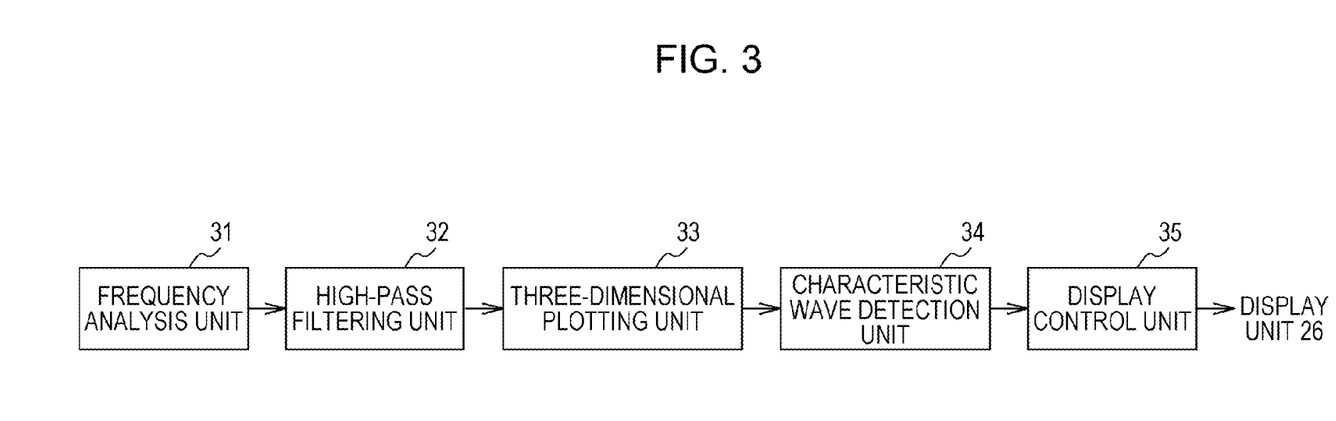
FIG. 3 is a block diagram illustrating the functional configuration of biological signal processing.

In this case, as illustrated in FIG. 3, the CPU 21 functions as a frequency analysis unit 31, a high-pass filtering unit 32, a three-dimensional plotting unit 33, a characteristic wave detection unit 34, and a display control unit 35.

The frequency analysis unit 31 performs a Fourier transform process or a wavelet transform process on a brain wave signal, and obtains the magnitude of each frequency component (hereinafter may be referred to as a spectrum) of a brain wave in each unit time. More specifically, the power spectrum (the ratio of energies of frequency components in each unit time) and/or the amplitude spectrum (the square root of the power spectrum) are obtained.

Figure 4A:
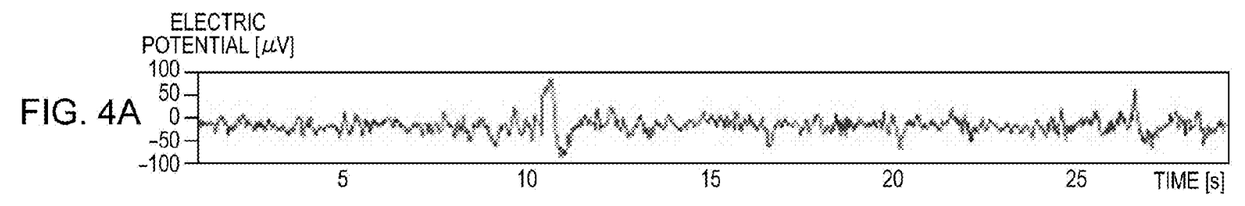
FIGS. 4A to 4C are graphs illustrating results (1) of an experiment.
Figure 4B:
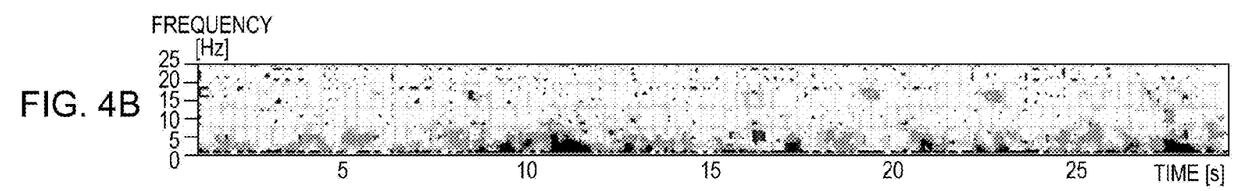

When the brain wave signal illustrated in FIG. 4A has been obtained as a result of an observation, the results of an analysis (elements of the spectrum) performed by the frequency analysis unit 31 are those illustrated in FIG. 4B when the results are plotted in a space defined by a time axis, a frequency axis, and an intensity axis. It is to be noted that the intensity axis illustrated in FIG. 4B is oriented in a direction perpendicular to the figure, and the unit used therefor is μV. In addition, in FIG. 4B, denser portions indicate higher intensities (electric potentials (amplitudes)).

The high-pass filtering unit 32 performs a high-pass filtering process on the spectrum in each unit time obtained by the frequency analysis unit 31 and extracts brain wave components having frequencies higher than a predetermined frequency.

More specifically, when the unit time is assumed to be t, the frequency is assumed to be f, and the spectrum (each element represented by a matrix at a time when a brain wave in each unit time x(t) is decomposed into each frequency component) obtained by the frequency analysis unit 31 is assumed to be S(f, t), the high-frequency components of the brain wave are weighted by multiplying each frequency component by the square root of the frequency component as in the following expression:

$$S' = f^{1/2} \cdot S \qquad (1)$$

As a result, components that would otherwise be buried among other components due to the attenuation of the brain wave can be highlighted.

The three-dimensional plotting unit 33 plots the spectrum (each element represented by a matrix and denoted by "S" in the above expression (1)) obtained as a result of the extraction performed by the high-pass filtering unit 32 in a space defined by a time axis, a frequency axis, and an intensity axis, thereby generating a brain wave pattern in a three-dimensional manner (hereinafter may be referred to as the three-dimensional brain wave pattern).

Figure 4C:
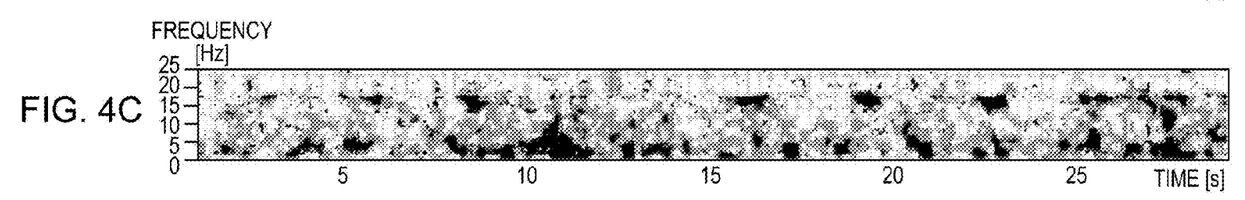

When the high-pass filtering process has been performed on the spectrum illustrated in FIG. 4B and the results of the high-pass filtering process have been plotted by the three-dimensional plotting unit 33 in a space defined by a time axis, a frequency axis, and an intensity axis, the spectrum illustrated in FIG. 4C is obtained. It is to be noted that the intensity axis and the unit used for the intensity axis in FIG. 4C are the same as those in FIG. 4B.

The characteristic wave detection unit 34 detects, from the three-dimensional brain wave pattern generated as a result of the plotting performed by the three-dimensional plotting unit 33, a brain wave component that is characteristic (hereinafter may be referred to as a characteristic brain wave component) and whose type has been specified as the target of recognition from among characteristic brain wave components.

Figure 5:
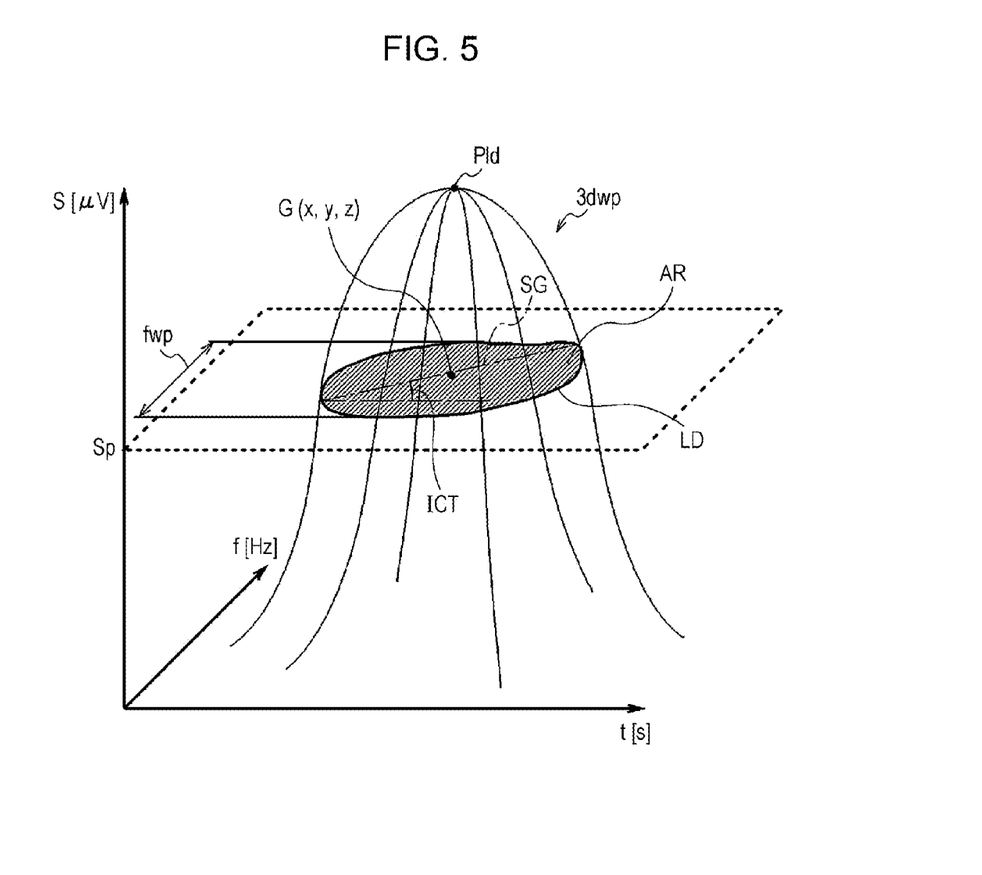
FIG. 5 is a graph illustrating standards for extracting a characteristic brain wave component.

As illustrated in FIG. 5, the standards for extracting a characteristic brain wave component herein include a position (hereinafter may be referred to as a particular value of intensity) Sp along the intensity axis at which a cross-section (hereinafter may be referred to as an island) LD of a three-dimensional brain wave pattern in the time-frequency domain is to be observed and the state of the island LD at the particular value of intensity Sp.

The particular value of intensity Sp is associated with each type of characteristic brain wave component and stored in the storage unit 27.

In this embodiment, the state of the island LD includes a frequency width, a position fwp of the frequency width, a center of gravity G, and an area AR, and the tolerances therefor are associated with the corresponding type of characteristic brain wave component and stored in the storage unit 27.

The particular value of intensity Sp is a value depending on the type of characteristic brain wave component. The frequency width of the island LD and the position fwp of the frequency width tend to be deviated from a particular frequency width and the position of the particular frequency width by a smaller amount as the amount by which components other than a characteristic brain wave component are superimposed becomes smaller.

The center of gravity G of the island LD tends to be deviated from the center by a smaller amount as the amount by which components other than the characteristic brain wave component are superimposed becomes smaller. The area AR of the island LD tends to be larger as the amount by which components other than the characteristic brain wave component are superimposed becomes larger, and tends to be smaller as the amount of attenuation of the brain wave signal becomes larger.

The types of characteristic brain wave components mainly include a delta wave (0.5 Hz to 4 Hz), a theta wave (4 Hz to 8 Hz), an alpha wave (8 Hz to 13 Hz), a beta wave (14 Hz to 30 Hz), and a spindle wave (12 to 14 Hz). In addition, a slow wave and a spike wave are also included.

A specific extraction method adopted by the characteristic wave detection unit 34 will be described hereinafter. In the first stage, the characteristic wave detection unit 34 reads, from the storage unit 27, for example, the tolerances of the particular value of intensity Sp, the frequency width, the position fwp of the frequency width, the center of gravity G, and the area AR that are associated with the type of characteristic brain wave component specified by the operation input unit 24 as the targets of recognition.

In the second stage, the characteristic wave detection unit 34 recognizes a single or a plurality of islands LD at the particular value of intensity Sp, which has been read from the storage unit 27, in the three-dimensional brain wave pattern, and detects the frequency widths, the positions fwp of the frequency widths, the centers of gravity G, and the areas AR of the islands LD.

Figure 6A:
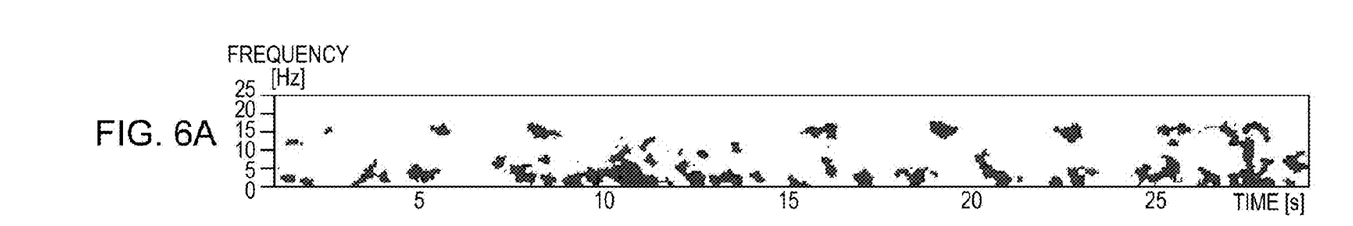
FIGS. 6A to 6C are graphs illustrating results (2) of an experiment.

When the three-dimensional brain wave pattern illustrated in FIG. 4C has been obtained, cross-sections (islands LD) in the time-frequency domain at a particular value of intensity Sp associated with a spindle wave are those illustrated in FIG. 6A.

In the third stage, the characteristic wave detection unit 34 detects, from among the single or the plurality of islands LD at the particular value of intensity Sp, which have been detected in the second stage, islands LD whose frequency widths, positions fwp of the frequency widths, centers of gravity G, and areas AR are all within the respective tolerances read from the storage unit 27 as the characteristic brain wave components to be recognized.

Figure 6B:
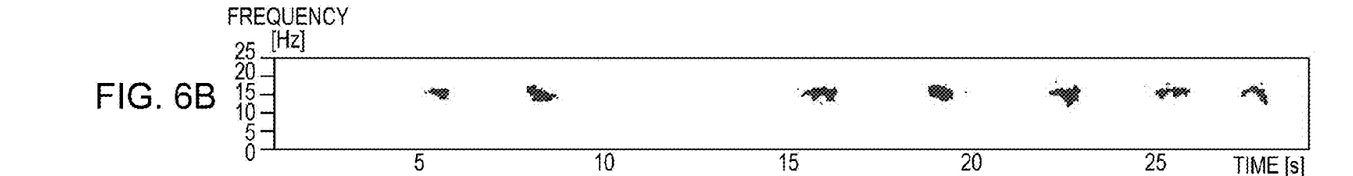

It is to be noted that when the islands LD illustrated in FIG. 6A have been obtained, the islands LD that have been detected, that is, the islands LD that are within the tolerances associated with the spindle wave, are ones illustrated in FIG. 6B.

The display control unit 35 displays, on the display unit 26, the entirety or a portion of a brain wave signal specified as the display target using the brain wave signal provided through the interface 25 in such a way that marks for indicating the presence of portions of a waveform corresponding to the islands LD detected by the characteristic wave detection unit 34 are attached to the brain wave signal.

Figure 6C:
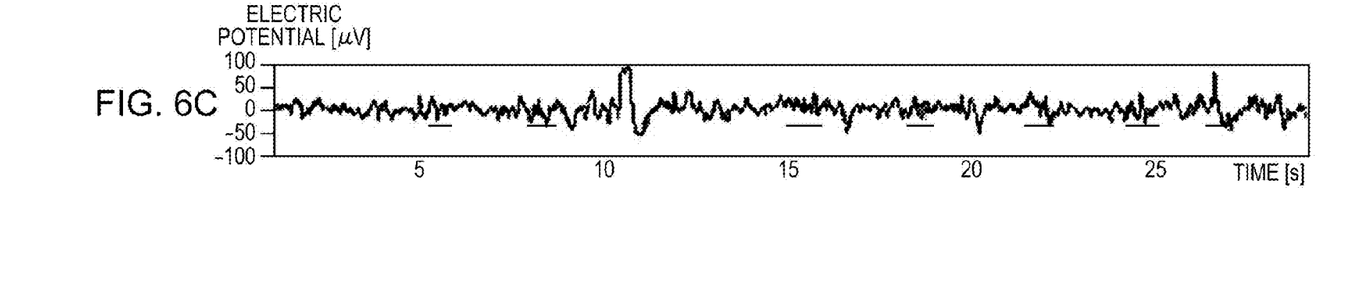

More specifically, for example, as illustrated in FIG. 6C, lines for indicating the presence of waveforms corresponding to the islands LD that match a specified characteristic brain wave component and that have been detected by the characteristic wave detection unit 34 are displayed in a color different from that of the brain wave signal. FIG. 6C illustrates the results of the observation illustrated in FIG. 4A and portions of a waveform corresponding to the islands LD illustrated in FIG. 6B.

1-4. Procedure for Brain Wave Processing

Figure 7:
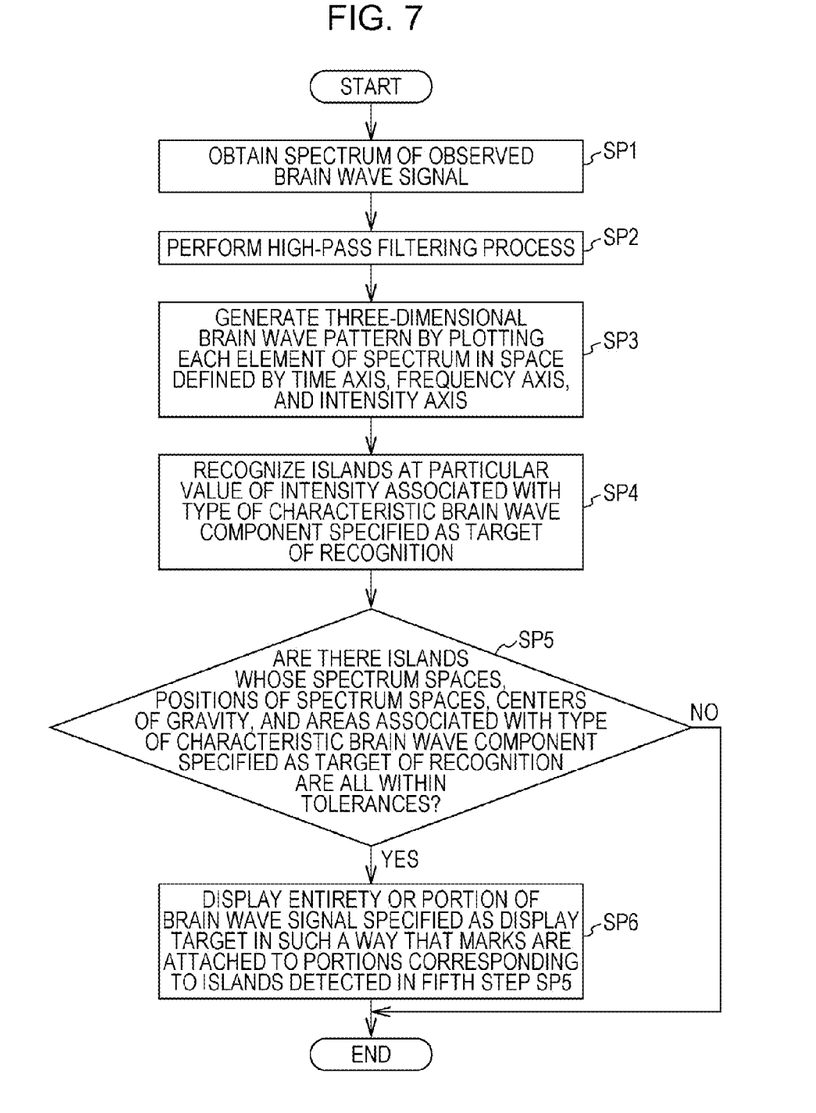
FIG. 7 is a flowchart illustrating the procedure for brain wave processing.

Next, the procedure for brain wave processing performed by the analysis unit 20 will be described with reference to the flowchart of FIG. 7.

Upon receiving a brain wave signal (FIG. 4A), the CPU 21 of the analysis unit 20 begins the procedure for the brain wave processing. The procedure proceeds to a first step SP1 and the spectrum of the brain wave signal is obtained (FIG. 4B). The procedure then proceeds to a second step SP2.

In the second step SP2, the CPU 21 performs a high-pass filtering process on the spectrum obtained in the first step SP1. The procedure proceeds to a third step SP3.

In the third step SP3, the CPU 21 generates a three-dimensional brain wave pattern (FIG. 4C) by plotting each element of the spectrum obtained in the second step SP2 as a result of the high-pass filtering process in a space defined by a time axis, a frequency axis, and an intensity axis. The procedure proceeds to a fourth step SP4.

In the fourth step SP4, the CPU 21 recognizes, in the three-dimensional brain wave pattern generated in the third step SP3, islands LD (FIG. 6A) at a particular value of intensity Sp associated with the type of characteristic brain wave component specified as the target of recognition. The procedure proceeds to a fifth step SP5.

In the fifth step SP5, the CPU 21 judges whether or not there are islands LD (FIG. 6B) whose frequency widths, positions fwp of the frequency widths, centers of gravity G, areas AR associated with the type of characteristic brain wave component specified as the target of recognition are all within the respective tolerances from among the islands recognized in the fourth step SP4.

If there are islands LD that are within the tolerances, the procedure proceeds to a sixth step SP6 and the CPU 21 displays, on the display unit 26, the entirety or a portion of the brain wave signal that has been observed in such a way that marks are attached to portions of the brain wave signal corresponding to the islands LD detected in the fifth step SP5 (FIG. 6C). The procedure for the brain wave processing then ends.

On the other hand, if there are no islands LD that are within the tolerances, the CPU 21 ends the procedure for the brain wave processing without performing the sixth step SP6.

1-5. Advantageous Effects

With the above-described configuration, the biological signal processing apparatus 1 plots the elements of the spectrum of an observed brain wave signal in a space defined by a time axis, a frequency axis, and an intensity axis, thereby generating a three-dimensional brain wave pattern (FIG. 4C).

In addition, the biological signal processing apparatus 1 detects the specified characteristic brain wave component using a position (a particular value of intensity Sp) along the intensity axis at which a cross-section (an island LD) of a three-dimensional brain wave pattern in the time-frequency domain is to be observed and the state of the cross-section at the position as the criteria for recognition (FIG. 5).

The biological signal processing apparatus 1 then displays, on the display unit 26, the entirety or a portion of the brain wave signal specified as the display target in such a way that marks for indicating the presence of portions of a waveform corresponding to the islands LD detected from the three-dimensional brain wave pattern are attached to the brain wave signal (FIG. 6C).

Since the characteristic brain wave pattern is detected using the state of the cross-section of the three-dimensional brain wave pattern at the particular value of intensity Sp plotted in the space defined by the time axis, the frequency axis, and the intensity axis as the criterion for recognition, waveform components can be recognized in a minute manner compared to when a characteristic brain wave pattern is detected from a plane in the time-frequency domain or the time-intensity domain.

More specifically, a particular value of intensity Sp, at which the cross-section (the island LD) is to be observed, depends on the type of specified characteristic brain wave component; however, the particular value of intensity Sp does not change even if an artifact has been superimposed.

On the other hand, the state of the cross-section (the island LD) at the particular value of intensity Sp undesirably changes in accordance with an artifact. However, it is highly unlikely that all the elements such as the position along the axis, the size, and the shape of the cross-section change, and it has been confirmed with the experiment illustrated in the drawings that at least one element, which is, for example, the position, the size, or the shape that depends on the specified characteristic brain wave component, is kept unchanged.

Therefore, by using the state of a cross-section of the three-dimensional brain wave pattern at a particular value of intensity Sp as the criterion for recognition, it is possible to recognize the specified characteristic brain wave component regardless of the type of artifact even if biological signals other than a brain wave are not obtained simultaneously. This is advantageous in terms of visual recognition of an observed waveform because the characteristic brain wave component can be recognized without expertise.

In addition, for example, if two types of characteristic brain wave components have been specified as the targets of recognition, the characteristic wave detection unit 34 searches for the states of cross-sections (islands LD) at a particular value of intensity Sp corresponding to each of the two characteristic brain wave components.

In this case, even if the two characteristic brain wave components are mixed in the same period of observation, the characteristics of the characteristic brain wave components can be observed with regard to at least one element, which is, for example, the position, the area, or the shape of a cross-section (an island LD) at the particular value of intensity Sp corresponding to each characteristic brain wave component. Therefore, the two characteristic brain wave components can be simultaneously recognized on the basis of the cross-sections (the islands LD) at the corresponding particular values of intensity Sp.

It is to be noted that, if two types of characteristic brain wave components have been specified as the targets of recognition, the display control unit 35 displays an observed brain wave signal in such a way that marks are attached to portions corresponding to the respective islands LD at the two types of particular values of intensity Sp detected by the characteristic wave detection unit 34.

Figure 8A:
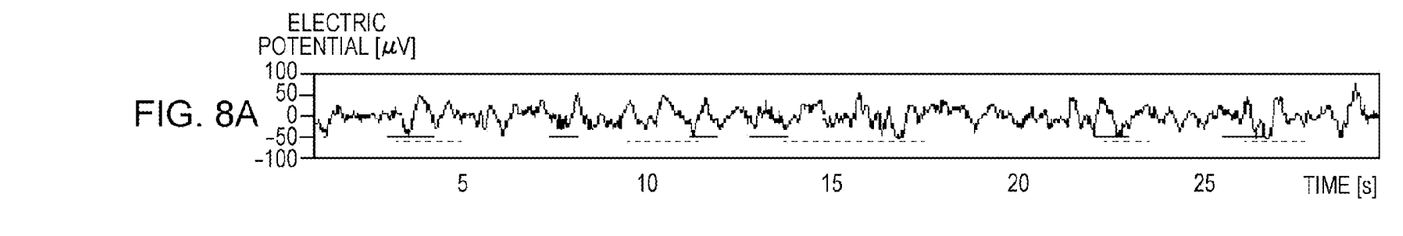
FIGS. 8A and 8B are outline diagrams illustrating an example of display at a time when two types of characteristic brain wave components have been specified as targets of recognition.
Figure 8B:
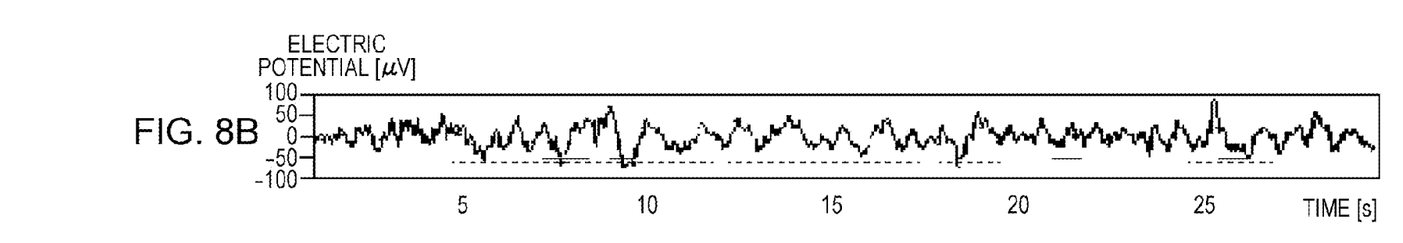

More specifically, as illustrated in FIGS. 8A and 8B, lines for indicating the presence of waveforms corresponding to the islands LD at the two types of particular values of intensity Sp detected by the characteristic wave detection unit 34 are displayed in colors different from each other and different from that of the brain wave signal. FIG. 8A illustrates a case in which an alpha wave and a spindle wave have been specified as the targets of recognition, and FIG. 8B illustrates a case in which an alpha wave and a slow wave have been specified as the targets of recognition.

As can be seen from FIGS. 8A and 8B, even if two characteristic brain wave components are mixed in the same period of observation, it is possible to simultaneously recognize the two characteristic brain wave components. This is significantly advantageous in terms of visual recognition of an observed waveform because the characteristic brain wave components can be recognized without expertise.

In addition, the processing is simple since the elements of a spectrum are plotted in a space defined by a time axis, a frequency axis, and an intensity axis and certain elements for recognition are compared with the tolerances without performing a special calculation process on the results of a frequency analysis. This is significantly advantageous in terms of the processing load and the like.

In addition, in this embodiment, in a stage before the elements of a spectrum are plotted in a space defined by a time axis, a frequency axis, and an intensity axis, a high-frequency component of the spectrum is weighted by a high-pass filtering process performed on the spectrum (FIG. 4B).

Therefore, a specified characteristic brain wave component that would otherwise be subjected to the attenuation of a brain wave or buried among other components is highlighted. As a result, the specified characteristic brain wave component can be recognized more accurately compared to when the high-pass filtering process is omitted, even if various artifacts have been superimposed.

In the configuration described above, waveform components can be recognized in a minute manner compared to when the waveform components are detected from a plane in the time-frequency domain or the time-intensity domain, which realizes the biological signal processing apparatus 1 with which the recognition accuracy of a particular waveform component can be improved.

2. Other Embodiments

In the above-described embodiment, a brain wave signal is adopted as the target of observation. However, the target of observation is not limited to that in the above-described embodiment. For example, a biological signal such as a myo-electric potential or an ocular potential that can be obtained by observing various waves transmitted from an organism as the targets of observation may be adopted.

In the above-described embodiment, the magnitude of frequency components (either or both a power spectrum and an amplitude spectrum) in each unit time is obtained. However, the target of obtainment may also include a phase spectrum.

In the above-described embodiment, a frequency width, a position fwp of the frequency width, a center of gravity G, and an area AR are adopted as the state of an island LD. However, the elements to be recognized as the state of the island LD are not limited to those in the above-described embodiment. For example, the shape of the island LD may be adopted. The shape tends to be closer to a circle (includes an ellipse) as the amount by which components other than a characteristic brain wave component are superimposed becomes smaller.

In addition, not only the state of the island LD, but also the state of a three-dimensional waveform portion 3dwP between the island LD and a peak Pld of a three-dimensional waveform including the island LD may be adopted as the criteria for recognition. More specifically, the three-dimensional waveform portion 3dwP may be, as illustrated in FIG. 5, a longest segment SG that can be obtained in the area of the island LD, an inclination ICT relative to the time axis, or the like. The inclination ICT tends to be larger as the amount by which components other than a characteristic brain wave component are superimposed becomes smaller.

Because waveform components can be recognized in a more minute manner when the state of the three-dimensional waveform portion 3dwP including the island LD is used as the criterion for recognition in addition to the state of the island LD, the recognition accuracy of a particular waveform component can be further improved.

It is to be understood that the content of the processing performed by the biological signal processing apparatus 1 may be modified even if the modification is not described in the above "Embodiment" and "Other Embodiments", so long as the scope of the present disclosure is not deviated from.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A biological signal processing apparatus comprising:
   an obtaining unit that obtains a spectrum of a biological signal that has been observed;
   a generation unit that generates a three-dimensional waveform by plotting elements of the spectrum obtained by the obtaining unit in a space defined by a time axis, a frequency axis, and an intensity axis; and
   a detection unit that detects a specified waveform component using a position along the intensity axis at which a cross-section of the three-dimensional waveform in a time-frequency domain generated by the generation unit is to be observed, and uses a state of the cross-section at the position as criteria for recognition of the specified waveform component, wherein the state of the cross-section includes at least one of a width of the cross-section along the frequency axis, a center of gravity of the cross-section, and an area of the cross-section.

2. The biological signal processing apparatus according to claim 1, further comprising:
   a weighting unit that weights a high-frequency component of the spectrum obtained by the obtaining unit,
   wherein the generation unit plots elements of the spectrum whose high-frequency component has been weighted by the weighting unit in a space defined by a time axis, a frequency axis, and an intensity axis.

3. The biological signal processing apparatus according to claim 2, further comprising:
   a display control unit that displays the entirety or a portion of the biological signal in such a way that a mark for indicating presence of a waveform component detected by the detection unit is attached.

4. The biological signal processing apparatus according to claim 3, wherein the biological signal is a brain wave signal.

5. The biological signal processing apparatus according to claim 2,
   wherein the detection unit also uses a state of a three-dimensional waveform located between the cross-section and a peak of a three-dimensional waveform that includes the cross-section as the criteria for recognition of the specified waveform component.

6. A biological signal processing method comprising:
   obtaining with an obtaining unit a spectrum of a biological signal that has been observed;
   generating with a generation unit a three-dimensional waveform by plotting elements of the spectrum obtained in the obtaining in a space defined by a time axis, a frequency axis, and an intensity axis; and
   detecting with a detection unit a specified waveform component using a position along the intensity axis at which a cross-section of the three-dimensional waveform in a time-frequency domain generated in the generating is to be observed and using a state of the cross-section at the position as criteria for recognition of the specified waveform component, wherein the state of the cross-section includes at least one of a width of the cross-section along the frequency axis, a center of gravity of the cross-section, and an area of the cross-section.

7. A non-transitory computer readable storage medium comprising a biological signal processing computer program product that causes a computer to:
   obtain a spectrum of a biological signal that has been observed;
   generate a three-dimensional waveform by plotting elements of the spectrum obtained in the obtaining in a space defined by a time axis, a frequency axis, and an intensity axis; and
   detect a specified waveform component using a position along the intensity axis at which a cross-section of the three-dimensional waveform in a time-frequency domain generated in the generating is to be observed and using a state of the cross-section at the position as criteria for recognition of the specified waveform component, wherein the state of the cross-section includes at least one of a width of the cross-section along the frequency axis, a center of gravity of the cross-section, and an area of the cross-section.

* * * * *